(12) United States Patent
Holmqvist

(10) Patent No.: US 8,708,973 B2
(45) Date of Patent: Apr. 29, 2014

(54) MEDICAMENT DELIVERY DEVICE POWERED BY VOLUTE SPRING

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 302 days.

(21) Appl. No.: 13/121,724

(22) PCT Filed: Sep. 30, 2009

(86) PCT No.: PCT/EP2009/062650
§ 371 (c)(1),
(2), (4) Date: Apr. 1, 2011

(87) PCT Pub. No.: WO2010/037759
PCT Pub. Date: Apr. 8, 2010

(65) Prior Publication Data
US 2011/0184351 A1    Jul. 28, 2011

(30) Foreign Application Priority Data
Oct. 1, 2008   (SE) .................................... 0850026-6

(51) Int. Cl.
*A61M 5/00*      (2006.01)
*A61M 5/32*      (2006.01)

(52) U.S. Cl.
USPC .......................... 604/211; 604/187; 604/198

(58) Field of Classification Search
USPC ............ 604/19, 48, 93.01, 131, 134, 187, 68, 604/63, 198, 211
See application file for complete search history.

(56) References Cited

U.S. PATENT DOCUMENTS

| | | | |
|---|---|---|---|
| 6,626,868 B1 * | 9/2003 | Prestidge et al. | 604/158 |
| 2002/0055712 A1 * | 5/2002 | Neracher | 604/143 |
| 2006/0270972 A1 * | 11/2006 | Lindmayer | 604/68 |

FOREIGN PATENT DOCUMENTS

| | | |
|---|---|---|
| DE | 2063786 A1 | 7/1972 |
| DE | 10237955 A1 | 3/2004 |
| FR | 2144105 A5 | 2/1973 |
| WO | 98/34659 A1 | 8/1998 |

OTHER PUBLICATIONS

EPO, Int'l Search Report in PCT/EP2009/062650, Dec. 17, 2009.
EPO, Written Opinion in PCT/EP2009/062650, Dec. 17, 2009.

* cited by examiner

*Primary Examiner* — Kami A Bosworth
*Assistant Examiner* — Imani Hayman
(74) *Attorney, Agent, or Firm* — Piedmont Intellectual Property

(57) ABSTRACT

The present invention relates to a medical delivery device comprising a housing (10); a medicament container (16) arranged to be placed in said housing; a stopper (18) movable within said container; a medicament dispensing means attachable to said housing and to said container through which medicament can be expelled; characterized in that the device further comprises a power unit (22) comprising a cover (24), a volute spring (26) arranged within said cover, and a pressure member (28) having a pressure pad (30) in contact with the stopper, a guide rod (34) extending into the volute spring and an annular ledge (32) in contact with the edges of the volute spring; activation means (36) mechanically connected to the cover and to the housing; and a spring locking means mechanically connected to said activation means, wherein said spring locking means (39) comprises a deformable ring-shaped member having (40) an inner diameter somewhat larger than the annular ledge, such that said ring-shaped member presents an oval shape when it is in contact with the annular ledge for locking the volute spring in a tensioned state.

3 Claims, 4 Drawing Sheets

MEDICAMENT DELIVERY DEVICE POWERED BY VOLUTE SPRING

TECHNICAL AREA

The present invention relates to a medicament delivery device capable of delivering doses of medicament in liquid form, and in particular injection medicament delivery devices.

TECHNICAL BACKGROUND

Medicament delivery devices developed for self-administration have become very popular because it allows for the users to provide medicament without the need for visiting a hospital, a clinic or the like in order to receive an injection of medicament.

The devices for self-administration that have been developed contain different degrees of functionality depending e.g. on the application, type of drug and intended user. The different functions may include automatic penetration, injection, mixing, priming, withdrawal from injection site, needle shields, to mention a few.

The majority of injection devices on the market are arranged with elongated, generally tubular medicament containers having one end where an injection needle can be attached, and provided with a movable wall at the other end, such as a rubber stopper. It is further very common to have some sort of elongated driver acting on said stopper, such as a plunger rod. The driver is also often connected to a power source such as compression springs, leaf springs, and the like for urging the plunger rod against the stopper for expelling medicament through the injection needle.

The use of plunger rods is very well developed and they be moved forward by the power source either linearly or rotatingly. A general desire from many users is to have as small devices as possible in order that they shall not attract too much attention, especially when the devices sometimes are to be used in the public. A problem with the above mentioned use of plunger rods is that the device has to be at least somewhat longer than the length of the medicament container plus the length of the plunger rod. The length problem becomes even more pronounced when functionality is added to the injector, such as dose setting buttons, needle shields extending from the injector, to mention some. The problem is also more pronounced the longer the plunger has to move inside the medicament container, either that the doses are large or that the injector is designed to deliver a number of doses before the container is emptied.

A few attempts have been made to solve this problem. One such solution is shown in document U.S. Pat. No. 6,641,566 where the power source is placed parallel to the medicament container. Here the plunger rod is designed flexibly bendable around a wheel in order that the power source can act on the container via the plunger rod. However, even if the device becomes shorter, by necessity it becomes thicker and also obtains a shape that is more difficult to hold for a user. This means that the device is not as discrete as desired. Further, many patients have by now gotten used to injectors having a general pen-shape and are thus reluctant to adapt to other shapes.

Another solution is shown in EP 1 647 292 A1 wherein the activation mechanism requires a rather complex design.

There is thus room for improvement regarding the size and design of injector.

BRIEF DESCRIPTION OF THE INVENTION

The aim of the present invention is to provide a medicament injector having dimensions that renders it as slim and compact as possible, and yet simple and robust to use.

This aim is obtained by an injector with the features according to the independent patent claims. Preferable embodiments form the subject of the dependent patent claims.

According to a main aspect of the invention, it is characterised by a medical delivery device comprising a housing; a medicament container arranged to be placed in said housing; a stopper movable within said container; a medicament dispensing means attachable to said housing and to said container through which medicament can be expelled; characterized in that the device further comprises a power unit comprising a cover, a volute spring arranged within said cover, and a pressure member having a pressure pad in contact with the stopper, a guide rod extending into the volute spring and an annular ledge in contact with the edges of the volute spring; activation means mechanically connected to the cover and to the housing; and a spring locking means mechanically connected to said activation means, wherein said spring locking means comprises a deformable ring-shaped member having an inner diameter somewhat larger than the annular ledge, such that said ring-shaped member presents an oval shape when it is in contact with the annular ledge for locking the volute spring in a tensioned state.

According to another aspect of the invention, the activation means is fixedly connected to the cover and rotationally operable in relation to the housing between a non-activation position wherein the activation button is in contact with a circumferential ledge of the housing for avoiding the activation button to be depressed, and an activation position wherein the activation button is in front of a cut-out on the circumferential ledge the housing for allowing the activation button to be depressed.

According to a further aspect of the invention, the activation means comprises an activation button operationally connected to said deformable ring-shaped member, such that when the cover is rotated from the non-activation position to the activation position, the deformable ring-shaped member is changed from the oval shape to a round shape, allowing the annular ledge to pass through the ring-shaped member and thereby releasing the volute spring from the tensioned state.

According to yet another aspect of the invention, said medicament dispensing means is an injection needle, a nozzle, a mouthpiece or the like.

There are a number of advantages with the present invention. The use of a volute spring provides a several features that conventional medical delivery devices do not provide. A major feature is that a plunger rod can be completely disposed of, which in conventional devices adds to the length. The use of a volute spring thus enables the device to be made much shorter; it is only the width of the band forming the volute spring that adds to the length. Because of its design the volute spring stays stable, i.e. does not buckle or twist, when it is extended, which is the case for conventional spiral springs. Thus the volute spring both acts as a force means and a "plunger rod" when extended. The width of the band forming the volute spring and the number of turns as well as choice of material may be modified in many ways in order to obtain the appropriate force, stability and stroke depending on application. In that respect, some sort of lubrication or friction reducing means may be applied on the band forming the spring in order to minimize friction when the spring extends.

With the present invention, a very simple but yet robust design with very few components is obtained for the spring locking means. The round shape of the volute spring can be used to hold the spring in the tensioned, non-extended state by using a ring-shaped member that in an unaffected state is somewhat oval. This ovality prevents the spring from extending. When the ring-shaped member is acted upon by manually operation, becoming circular, it enables the volute spring to expand through the member. Further, the present invention preferably includes a safety lock of the spring locking means, which reduces the risk of unintentional activation of the medicament delivery device.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
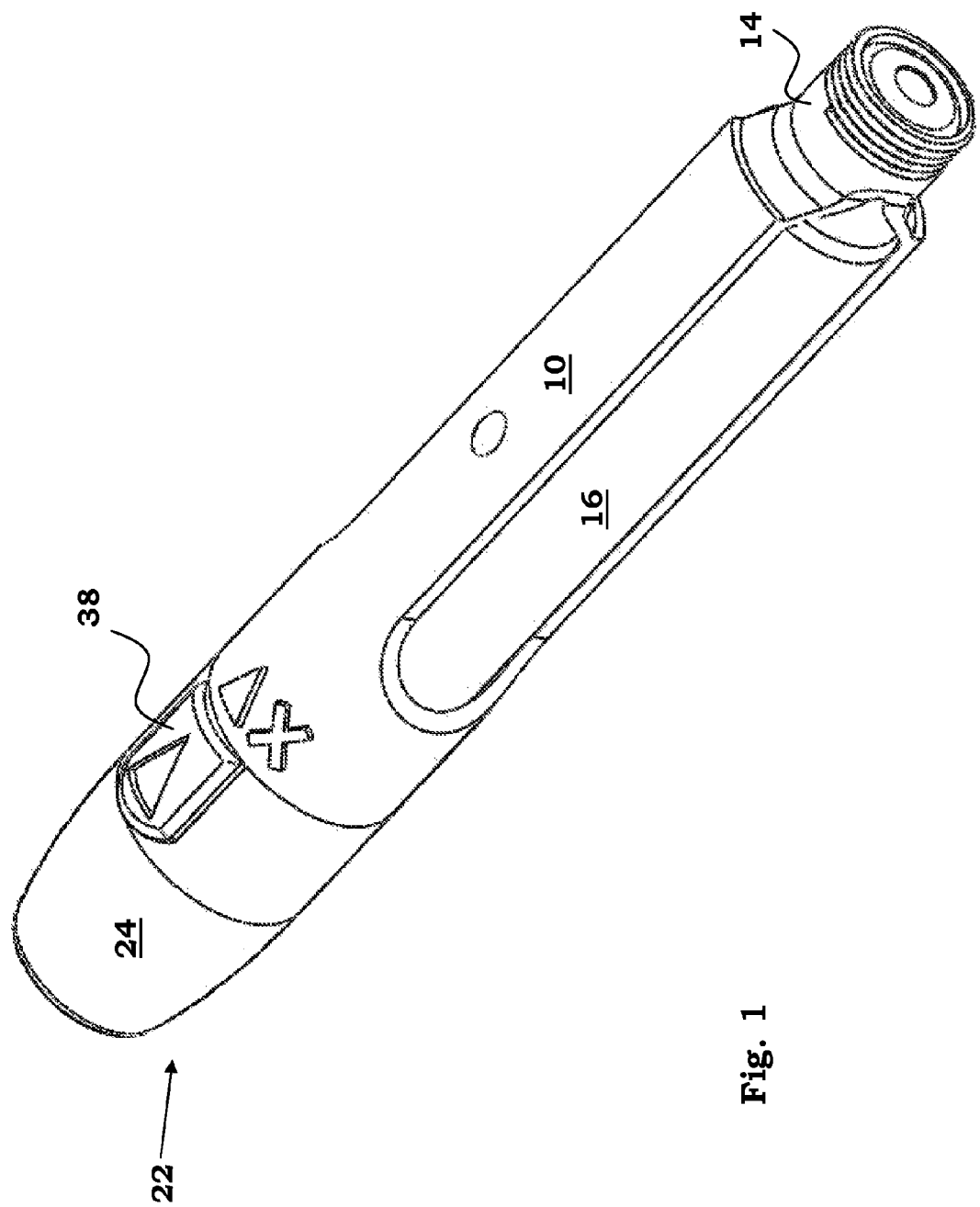
FIG. 1 is a perspective view of a medicament delivery device according to the present invention.
Figure 2:
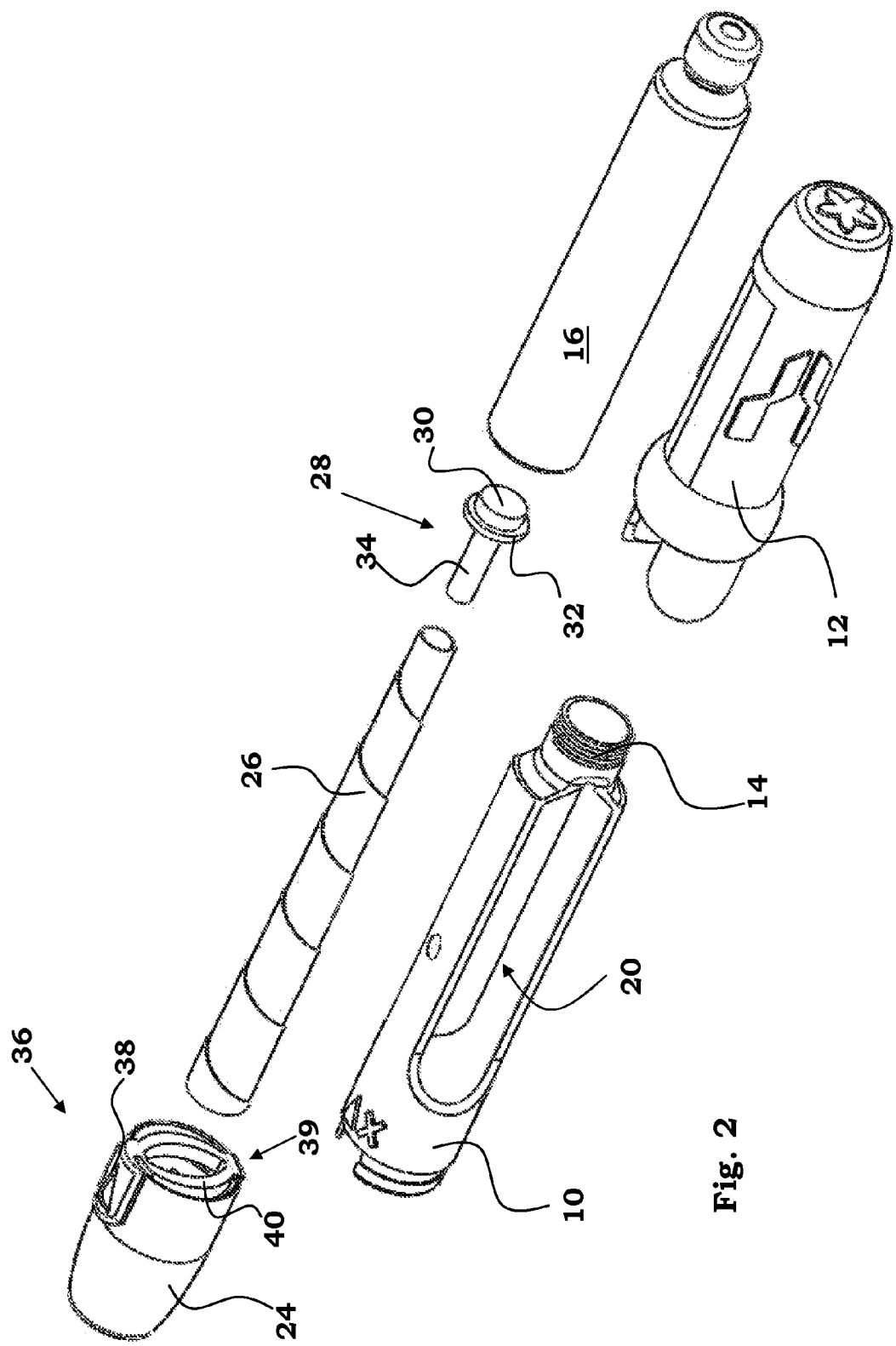
FIG. 2 is an exploded view of the medicament delivery device of FIG. 1, and FIGS. 3, 4 are cross-sectional side views of the device of FIG. 1.
Figure 3:
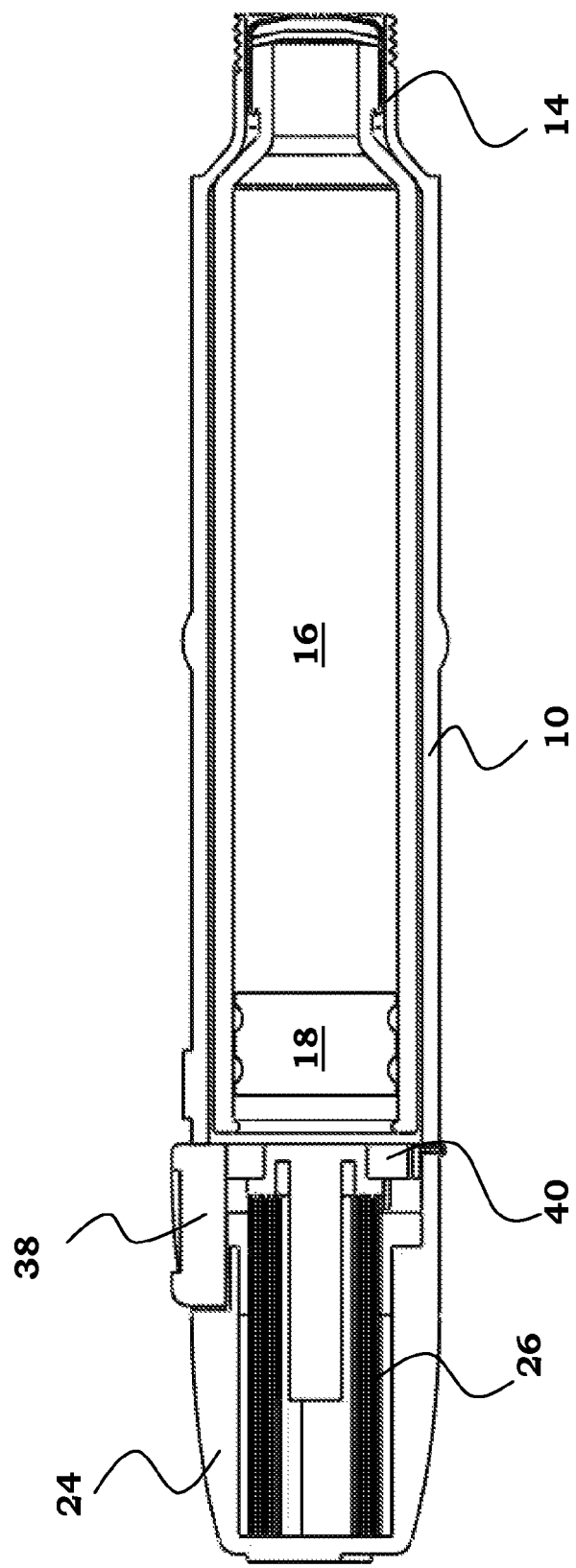
Figure 4:
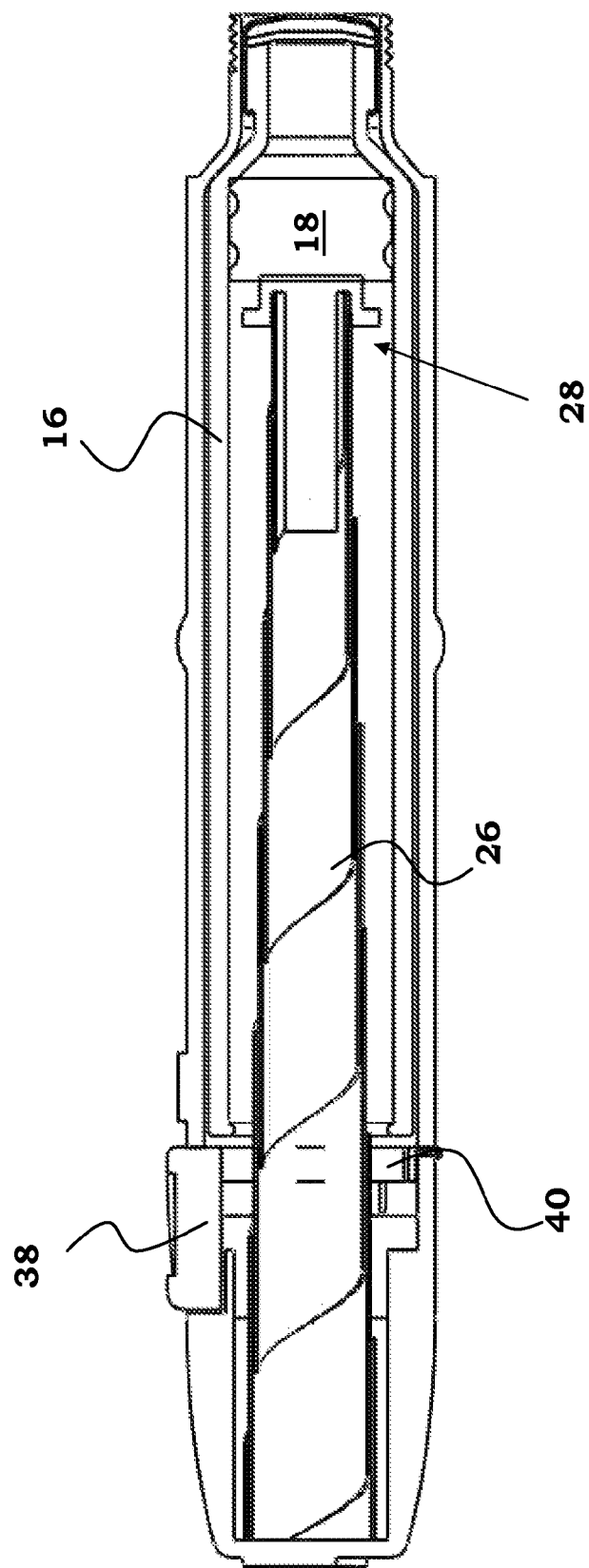

The medicament delivery device shown in the drawings comprises an elongated, generally tubular housing 10. When the device is delivered to the user, the front part of the housing is covered by a detachable protective cover 12, FIG. 2. The front end of the housing 10, to the right in the figures, is provided with a threaded neck 14 onto which a medicament dispensing means such as an injection needle, a nozzle, a mouthpiece or the like can attached. Inside the housing, a medicament container 16 is placed. The front end of the container is placed in the neck 14 of the housing. In the rear part of the medicament container a stopper 18 is arranged, FIGS. 3 and 4. The container 16 is visible through openings or windows 20 in the housing.

The rear part of the medicament delivery device is arranged with a power unit 22. It comprises a cover 24, a volute spring 26 arranged within said cover and that is wound with a number turns, and a pressure member 28 having a pressure pad 30 in contact with the stopper 18, a guide rod 34 extending into the volute spring and an annular ledge 32 in contact with the edges of the volute spring. The volute spring has a certain width as will be described below.

The device further comprises an activation means 36 mechanically connected to the cover (24) and to the housing (10). In the embodiment of the figures the activation means 36 is fixedly connected to the cover 24 and rotationally operable in relation to the housing 10 between a non-activation position wherein the activation button 38 is in contact with a circumferential ledge of the housing for avoiding the activation button to be depressed, and an activation position wherein the activation button is in front of a cut-out on the circumferential ledge of the housing for allowing the activation button to be depressed. The activation means comprises an activation button 38 which can be operated by a user. The activation button is in turn operationally connected to a spring locking means 39 which comprises a deformable ring-shaped member 40 having an inner diameter somewhat larger than the annular ledge 32 of the pressure member, such that said ring-shaped member 40 presents an oval shape when it is in contact with the annular ledge 12 for locking the volute spring in a tensioned state.

The activation button 38 is operationally connected to said deformable ring-shaped member 40, such that when the cover 24 is rotated from the non-activation position to the activation position, the deformable ring-shaped member 40 is changed from the oval shape to a round shape, allowing the annular ledge 32 to pass through the ring-shaped member and thereby releasing the volute spring from the tensioned state.

The medicament delivery device according to the present invention is intended to function as follows. When the patient is to administer a dose of medicament, a medicament container 16 is placed in the housing and the cover part 24 is attached to the housing. As an alternative, the device may be delivered to the user with a medicament container already in place in the housing.

Now a medicament dispensing means is attached to the neck 14 of the housing 10 by appropriate fastening means such as threads or bayonet fittings. In order to make the device ready for medicament delivery the cover and thereby the activation means are turned from the non-activation position to the activation position. The device is after this positioned at the medicament delivery site, such as penetration of an injection needle at the injection place, or in, or adjacent the mouth or nose when a nozzle is used. The activation button 38 is now pressed by the user whereby the deformable ring-shaped member 40 is changed from the oval shape to the round shape. The change of shape causes the deformable ring-shaped member 40 to move out of contact with the circumferential ledge 32 of the pressure member 28, which enables the pressure member 28 and the volute spring 26 to move through the deformable ring-shaped member 40 and to extend in the longitudinal direction of the device, where the pressure pad 30 acts on the stopper of the medicament container 16. The force of the volute spring 26 now pushes the stopper 18 towards the front end of the medicament container 16 whereby the dose of medicament in the container is expelled through the medicament delivery means and into the delivery site. Due to the width of the band forming the volute spring 26, it becomes stable enough to exert a force on the stopper 18 through the whole injection phase without the risk of buckling or twisting, FIG. 4.

When the delivery operation is completed, the user removes the medicament delivery device. If the device is an injector, the user preferably covers the needle with the needle sheath. The needle can then be removed and discarded. The injector may be used again by replacing the empty container with a new and by replacing the used power unit 22 with a new for a subsequent use or the injector may be designed as a single use injector and discarded after completed injection. Even though a manually operated activation of the medicament delivery device has been described, it is to be understood that different types of automated activations are possible within the scope of the invention. In that respect, there may be a number of different designs regarding locking and holding the volute spring in the tensioned state.

It is to be understood that the embodiments described above and shown in the drawings are to be regarded only as non-limiting examples of the invention and that it may be modified in many ways within the scope of the patent claims.

The invention claimed is:

1. A medical delivery device, comprising:
 a housing;
 a medicament container arranged to be placed in the housing;
 a stopper movable within the container;

a medicament dispensing device attachable to the housing and the container through which medicament can be expelled, wherein the medicament dispensing device is an injection needle;

a power unit, comprising a cover, a single volute spring arranged within the cover, and a pressure member having a pressure pad in contact with the stopper, a guide rod extending into the volute spring and an annular ledge in contact with the edges of the volute spring;

an activation mechanism mechanically connected to the cover and to the housing; and a spring locking mechanism mechanically connected to the activation mechanism, wherein the spring locking mechanism comprises a deformable ring-shaped member having an inner diameter larger than the annular ledge, such that the ring-shaped member presents an oval shape when it is in contact with the annular ledge for locking the volute spring in a tensioned state.

2. The medical delivery device of claim 1, wherein the activation mechanism is fixedly connected to the cover and rotationally operable in relation to the housing between a non-activation position, in which an activation button is in contact with a circumferential ledge of the housing for avoiding the activation button to be depressed, and an activation position, in which the activation button is in front of a cut-out on the circumferential ledge of the housing for allowing the activation button to be depressed.

3. The medical delivery device of claim 2, wherein the activation mechanism comprises an activation button operationally connected to the deformable ring-shaped member, such that when the cover is rotated from the non-activation position to the activation position, the deformable ring-shaped member is changed from the oval shape to a round shape, allowing the annular ledge to pass through the ring-shaped member and thereby releasing the volute spring from the tensioned state.

* * * * *